(12) United States Patent
Luo et al.

(10) Patent No.: US 7,736,313 B2
(45) Date of Patent: Jun. 15, 2010

(54) DETECTING AND CLASSIFYING LESIONS IN ULTRASOUND IMAGES

(75) Inventors: Jiebo Luo, Pittsford, NY (US); Zhimin Huo, Pittsford, NY (US); Wei Hao, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 588 days.

(21) Appl. No.: 10/994,794

(22) Filed: Nov. 22, 2004

(65) Prior Publication Data

US 2006/0120608 A1 Jun. 8, 2006

(51) Int. Cl.
*A61B 8/00* (2006.01)

(52) U.S. Cl. .................. 600/437; 382/128; 382/133; 382/224; 345/581; 345/589; 345/618; 128/922

(58) Field of Classification Search .............. 600/437, 600/440, 443, 447, 458, 425; 382/128, 224, 382/130–132, 133; 345/581, 618, 589, 599, 345/641, 690; 128/920, 922
See application file for complete search history.

(56) References Cited

U.S. PATENT DOCUMENTS

| | | | | |
|---|---|---|---|---|
| 5,016,173 A | * | 5/1991 | Kenet et al. .................. 382/128 |
| 5,671,294 A | * | 9/1997 | Rogers et al. ................ 382/228 |
| 5,825,909 A | | 10/1998 | Jang | |
| 5,832,103 A | * | 11/1998 | Giger et al. .................. 382/130 |
| 5,984,870 A | | 11/1999 | Giger et al. | |
| 6,138,045 A | * | 10/2000 | Kupinski et al. ............. 600/425 |
| 6,185,320 B1 | * | 2/2001 | Bick et al. ................... 382/132 |
| 6,208,749 B1 | * | 3/2001 | Gutkowicz-Krusin et al. ............... 382/128 |
| 6,282,305 B1 | | 8/2001 | Huo et al. | |
| 6,317,617 B1 | | 11/2001 | Gilhuijs et al. | |
| 6,537,211 B1 | * | 3/2003 | Wang et al. .................. 600/160 |
| 6,574,304 B1 | * | 6/2003 | Hsieh et al. ................... 378/62 |
| 6,697,502 B2 | * | 2/2004 | Luo ............................ 382/115 |
| 6,853,318 B1 | | 2/2005 | Rabbani et al. | |
| 6,855,114 B2 | * | 2/2005 | Drukker et al. ............. 600/443 |
| 6,901,156 B2 | | 5/2005 | Giger et al. | |
| 6,956,975 B2 | | 10/2005 | Young | |
| 7,035,461 B2 | | 4/2006 | Luo et al. | |

(Continued)

FOREIGN PATENT DOCUMENTS

EP 1 398 721 3/2004

OTHER PUBLICATIONS

J Luo, RT Gray, H-C Lee. Towards physics-based segmentation of photographic color images. Proceedings of the 1997 International Conference on Image Processing (ICIP '97), p. 58, 1997.*

(Continued)

*Primary Examiner*—Brian Casler
*Assistant Examiner*—Amanda Lauritzen (57) ABSTRACT

A method for determining a candidate lesion region within an ultrasound image. The method includes the steps of: accessing a digital ultrasound image of anatomical tissue; segmenting spatially contiguous pixels in the ultrasound image into a plurality of regions in accordance with substantially similar intensity values and spatial smoothness constraints; and selecting, from the plurality of regions, one or more candidate lesion regions having an intensity value lower than a predetermined intensity value. In one arrangement, the one or more candidate lesion region is classified into at least one of the following classes: benign, malignant, or unknown.

18 Claims, 6 Drawing Sheets

U.S. PATENT DOCUMENTS

| | | |
|---|---|---|
| 7,062,085 B2 | 6/2006 | Luo et al. |
| 7,123,762 B2 | 10/2006 | Giger et al. |
| 7,139,437 B2 | 11/2006 | Jones et al. |
| 7,171,058 B2 | 1/2007 | Luo |
| 7,221,787 B2 | 5/2007 | Luo et al. |
| 7,346,209 B2 * | 3/2008 | Gokturk et al. .............. 382/159 |
| 2003/0125621 A1 | 7/2003 | Drukker et al. |
| 2003/0161513 A1 | 8/2003 | Drukker et al. |
| 2004/0052328 A1 * | 3/2004 | Sabol et al. ................... 378/37 |
| 2004/0228529 A1 * | 11/2004 | Jerebko et al. .............. 382/173 |
| 2005/0010445 A1 * | 1/2005 | Krishnan et al. ................ 705/2 |
| 2005/0027188 A1 * | 2/2005 | Metaxas et al. ............. 600/410 |
| 2005/0105776 A1 | 5/2005 | Luo et al. |
| 2005/0123180 A1 | 6/2005 | Luo et al. |
| 2006/0018548 A1 * | 1/2006 | Chen et al. .................. 382/190 |
| 2006/0050958 A1 * | 3/2006 | Okada et al. ................ 382/173 |
| 2006/0098889 A1 | 5/2006 | Luo et al. |
| 2006/0110018 A1 | 5/2006 | Chen et al. |
| 2006/0110035 A1 | 5/2006 | Luo et al. |
| 2006/0110068 A1 * | 5/2006 | Luo et al. .................... 382/289 |
| 2006/0122480 A1 * | 6/2006 | Luo et al. .................... 600/407 |
| 2006/0228015 A1 * | 10/2006 | Brockway et al. ........... 382/132 |
| 2006/0245629 A1 * | 11/2006 | Huo et al. .................... 382/131 |
| 2006/0247525 A1 * | 11/2006 | Huo et al. .................... 600/437 |
| 2007/0165924 A1 | 7/2007 | Nicponski |

OTHER PUBLICATIONS

Jiebo Luo et al., "Towards Physics-based Segmentation of Photographic Color Images", 1997, IEEE Proceedings, pp. 58-61.

Zhimin Huo et al., Computer-Aided Diagnosis: Analysis of Mammographic Parenchymal Patterns and Classification of Masses on Digitized Mammograms, Proceedings of the 20th Annual International Conference of the IEEE Engineering in Medicine and Biology Society, vol. 20, No. 2, 1998, pp. 1017-1020.

S.G. Armato III et al., Computerized detection of lung nodules in computed tomography scans, Computer-Aided Diagnosis in Medical Imaging, pp. 119-123.

* cited by examiner

DETECTING AND CLASSIFYING LESIONS IN ULTRASOUND IMAGES

FIELD OF THE INVENTION

The invention relates to digital image processing of ultrasound images, and more particularly to detecting and classifying lesions within such images.

BACKGROUND OF THE INVENTION

Breast cancer risk assessment provides an opportunity to devise surveillance plans that may include enhanced screening for individuals at increased risk of breast cancer. Computerized analysis of mammographic parenchymal patterns may provide an objective and quantitative characterization and classification of these patterns, which may be associated with breast cancer risk. Computerized assessment of breast cancer risk that are based on the analysis of mammograms alone or combined with epidemiologic risk factors (for example, age) can serve as an alternative to current existing clinical methods, which are costly and/or information-dependent, in predicting breast cancer risk.

The breast is composed primarily of two components: fibroglandular tissue and fatty tissue. An average breast is comprised of 50% fibroglandular tissue and 50% fat. Fibroglandular tissue is a mixture of fibrous connective tissue and the glandular epithelial cells that line the ducts of the breast (the parenchyma).

Major breast diseases develop from the terminal ductal lobular units of the breast, and arise predominantly from the epithelial cells that line the ducts. However, the fibrous or connective tissue can also be involved. It is thought by some individuals that malignant breast disease develops through a process that starts with epithelial hyperplasia, i.e., an increase in the number of epithelial cells. Epithelial hyperplasia can progress to atypical hyperplasia in which the epithelial cells not only increase in number, but also change in a way that is not normal for these cells. The process, at this stage, is believed to be reversible. Once a certain criterion level of atypia is reached, the diagnosis of carcinoma-in-situ can be made, in which there is no invasion of malignant cells outside of the duct. The process of malignant transformation is considered irreversible at this stage. In the last phase of development, the cancer cells break out of the ductal walls and invade the surrounding stromal tissue, and at this point the disease is called infiltrating or invasive carcinoma.

Most (80%-85%) breast carcinomas can be seen on a mammogram as a mass, a cluster of tiny calcifications, or a combination of both. Other mammographic abnormalities are of lesser specificity and prevalence than masses and/or calcifications, and include skin or nipple changes, abnormalities in the axilla, asymmetric density, and architectural distortion.

Early detection of breast cancer can improve survival rates. Some statistics indicate that the overall five-year survival rate for women diagnosed with breast cancer is 84%, but when found at a small, localized stage, the 5-year survival rate is 97%. At least one study has shown that the use of screening mammography can reduce lesion size and stage at detection, improving the prognosis for survival. Currently, mammography is an established imaging technique for early detection of breast cancer. At least one organization has recommended annual screening mammography for all women over the age of 40.

U.S. Pat. No. 6,282,305 (Huo et al) is directed to a method and system for the computerized assessment of breast cancer risk, wherein a digital image of a breast is obtained and at least one feature is extracted from a region of interest in the digital image. The extracted features are compared with a predetermined model associating patterns of the extracted features with a risk estimate derived from corresponding feature patterns associated with a predetermined model based on gene carrier information or clinical information, or both gene carrier information and clinical information, and a risk classification index is output as a result of the comparison. Preferred features to be extracted from the digital image include 1) one or more features based on absolute values of gray levels of pixels in said region of interest, 2) one or more features based on gray-level histogram analysis of pixels in said region of interest; 3) one or more features based on Fourier analysis of pixel values in said region of interest; and 4) one or more features based on a spatial relationship among gray levels of pixels within the region of interest.

U.S. Pat. No. 5,984,870 (Giger et al.) is directed to a method for the analysis of a lesion existing in anatomical tissue, comprising the steps of (a) obtaining first digital image data derived from an ultrasound image of the anatomical tissue in which the lesion exists; (b) determining a location of the lesion in relation to the first digital data; (c) selecting for feature extraction analysis at least one of 1) a region of interest on the margin of the lesion, and 2) a region of interest which includes the lesion and a region of interest which is in the surrounding vicinity of the lesion, and 3) a region of interest which includes the lesion and a region of interest which is on the margin of the lesion; (d) extracting from each selected region of interest selected in said selecting step at least one first feature that characterize a lesion within said first image data; and (e) characterizing said lesion based on the extracted at least one first feature.

US Patent Applications No. 2003/0161513 and 2003/0125621 describe similar systems, using analysis of lesion shadows in an ultrasound image and a radial gradient index (RGI) feature in a sonographic image, respectively.

A difficulty associated with a computerized system for detecting and diagnosing breast lesions is segmentation of the lesion regions from the surrounding tissues. Some systems assume that segmentation is obtained by manual outlining the lesions using a graphic user interface, for example, U.S. Pat. No. 5,984,870 (Giger et al.). This manual procedure is labor-intensive, can disrupt full automation, and can be prone to human error, inconsistency and subjectivity. The resulting inaccuracy in the outline of the lesion has adverse effect on the subsequent computerized diagnosis because features computed from inaccurate lesion outline (e.g., those taught by U.S. Pat. No. 5,984,870 (Giger et al.)), tend to be inaccurate for lesion classification.

Accordingly, it is desirable to devise an automatic segmentation module to streamline the computerized mammography analysis system.

Pixel-based, edge-based, region-based, and model-based segmentation techniques are known in medical image processing. Each approach has its own limitations. For example, pixel-based segmentation techniques tend to have difficulties when there is a significant amount of noise in the image; edge-based techniques tend to experience problems when the boundary of the object is not well defined and when the image contrast is poor; while model-based techniques tend to fail when there is a significant amount of variation in the shape and appearance of the object of interest. Region-growing techniques require a good seed point (typically provided by manual interaction) and are subject to critical errors when adjoining objects closely match an object of interest in their appearance.

As such, there exists a need for a method which overcomes the limitations of existing methods.

The present invention provides a lesion segmentation and classification method wherein segmentation is automatic and relatively insensitive to variations in image noise and target appearance (color and shape). Further, the methods can provide a fully automatic system for segmenting and classifying lesions by cascading automatic lesion segmentation and automatic lesion classification.

SUMMARY OF THE INVENTION

An object of the present invention is to provide an lesion segmentation method in which segmentation is automatic and relatively insensitive to variations in image noise and target appearance (e.g., color and shape).

Another object of the present invention is to provide an automatic system for segmenting and classifying lesions by cascading automatic lesion segmentation and automatic lesion classification.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

The present invention provides a method, computer program, and system, in which a lesion region is automatically located within an ultrasound (mammographic) image, and such a lesion region is classified according to a plurality of features computed upon the lesion region itself to decide whether the lesion is benign or malignant.

It is an advantageous effect of the invention that an improved lesion diagnosis method and apparatus is provided, in which segmentation is automatic and is relatively insensitive to in image noise and target appearance (e.g., color and shape).

It is a further advantageous effect of the invention to provide a fully automated lesion segmentation and classification method.

According to one aspect of the present invention there is provided a method for determining a candidate lesion region within an ultrasound image. The method includes the steps of: accessing a digital ultrasound image of anatomical tissue; segmenting spatially contiguous pixels in the ultrasound image into a plurality of regions in accordance with substantially similar intensity values and spatial smoothness constraints; and selecting, from the plurality of regions, one or more candidate lesion regions having an intensity value lower than a pre-determined intensity value. In one arrangement, the one or more candidate lesion region is classified into at least one of the following classes: benign, malignant, or unknown.

BRIEF DESCRIPTION OF THE DRAWINGS

The above-mentioned and other features and objects of this invention and the manner of attaining them will become more apparent and the invention itself will be better understood by reference to the following description of an embodiment of the invention taken in conjunction with the accompanying figures wherein.

DETAILED DESCRIPTION OF THE INVENTION

The following is a detailed description of the preferred embodiments of the invention, reference being made to the drawings in which the same reference numerals identify the same elements of structure in each of the several figures.

Some portions of the detailed descriptions which follow are presented in terms of algorithms and symbolic representations of operations on data bits within a computer memory. These algorithmic descriptions and representations are used by those skilled in the data processing arts to most effectively convey the substance of their work to others skilled in the art. An algorithm is, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. For convenience, these signals as sometimes referred to herein in relation to the underlying information using referents such as bits, values, elements, symbols, characters, terms, numbers, or the like.

It should be recognized, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar data processing device, that manipulates and transforms data represented as physical (e.g. electronic) quantities within the computer system's registers and memories into other data similarly represented as physical quantities within the computer system memories or registers or other such information storage, transmission or display devices.

The present invention also relates to systems including specific pieces of apparatus for performing the operations described herein. Apparatus such as a programmable computer may be specially constructed for the required purposes, or may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs) such as Dynamic RAM (DRAM), EPROMs, EEPROMs, magnetic or optical cards, or any type of media suitable for storing electronic instructions, and each of the above storage components is coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the methods. The structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

References to "in a particular embodiment" and the like refer to features that are present in at least one embodiment of the invention. Separate references to "an embodiment" or "particular embodiments" or the like do not necessarily refer to the same embodiment or embodiments; however, such embodiments are not mutually exclusive, unless so indicated or as are readily apparent to one of skill in the art. The invention is thus inclusive of combinations of the embodiments described herein.

The term "lesion" is used herein to refer to a single abnormal mass within otherwise normal anatomical tissue.

The term "mammographic image" is used herein to refer to an image that shows a portion of a patient's breast, which includes normal breast tissue and in some cases lesions.

Elements not specifically shown or described herein may be selected from those known in the art. Certain aspects of the embodiment to be described may be provided in software. Given the method as shown and described according to the invention in the following materials, software not specifically shown, described or suggested herein that is useful for implementation of the invention is conventional and within the ordinary skill in such arts. The method of the invention is useful with, but not limited to, use with color image processing procedures well known to those of skill in the art.

Figure 1:
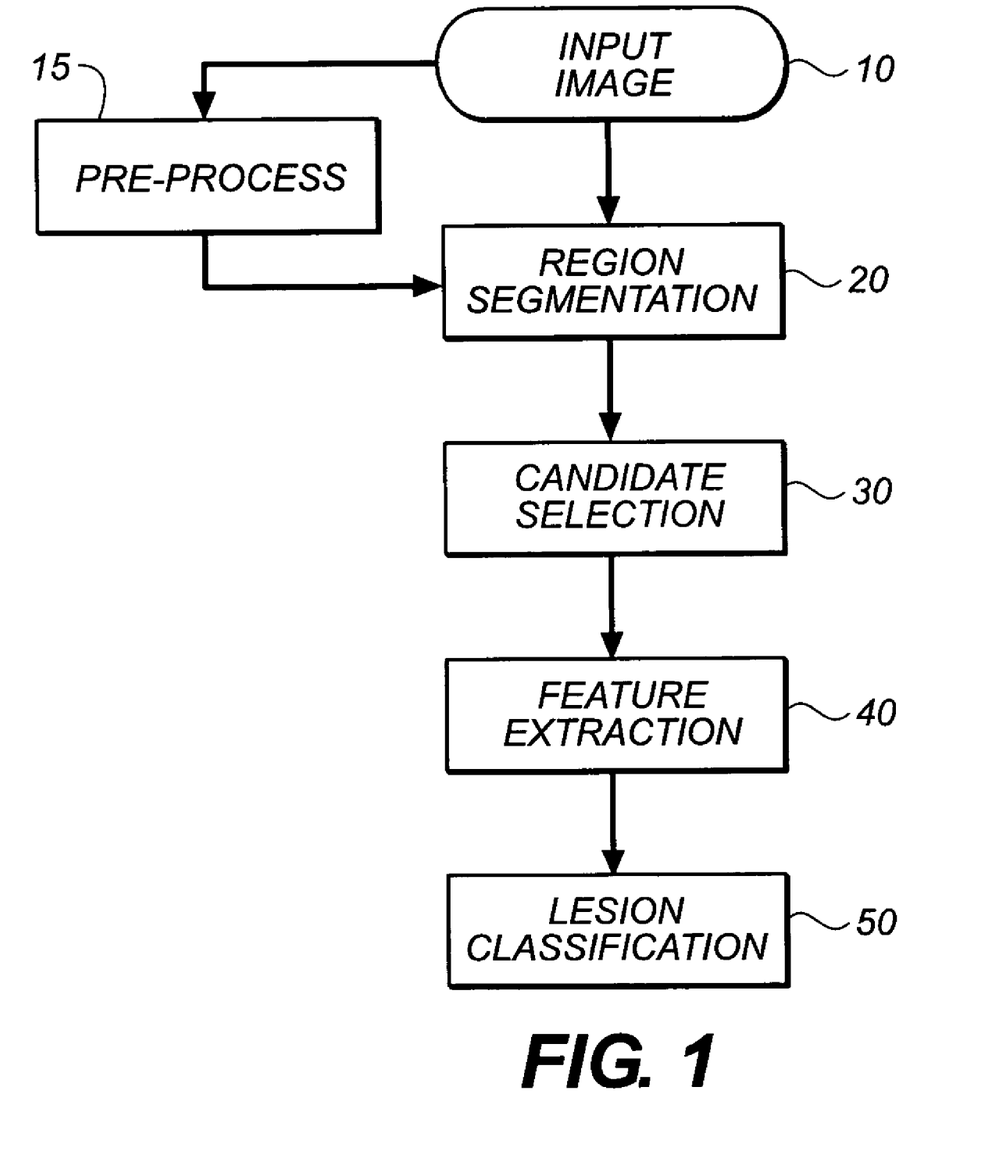
FIG. 1 is a block diagram illustrating the steps of an embodiment of the method in accordance with the present invention.

Referring to FIG. 1, the present invention is described with reference to the shown block diagram. First, an input ultrasound image 10 is accessed/acquired/provided for analysis. Region segmentation 20 is performed on the input ultrasound image to produce a number of regions, each having a distinctive intensity characteristic. Among segmented regions, some may be selected as candidate regions 30 for lesions. Next, a plurality of features are extracted 40 for each candidate region. Each candidate region is then classified 50, for example, as a benign lesion, or a malignant lesion, or in some cases, not a lesion.

As will be more particularly described below, it may be desirable to pre-process 15 the input image prior to region segmentation 20.

Figure 2:
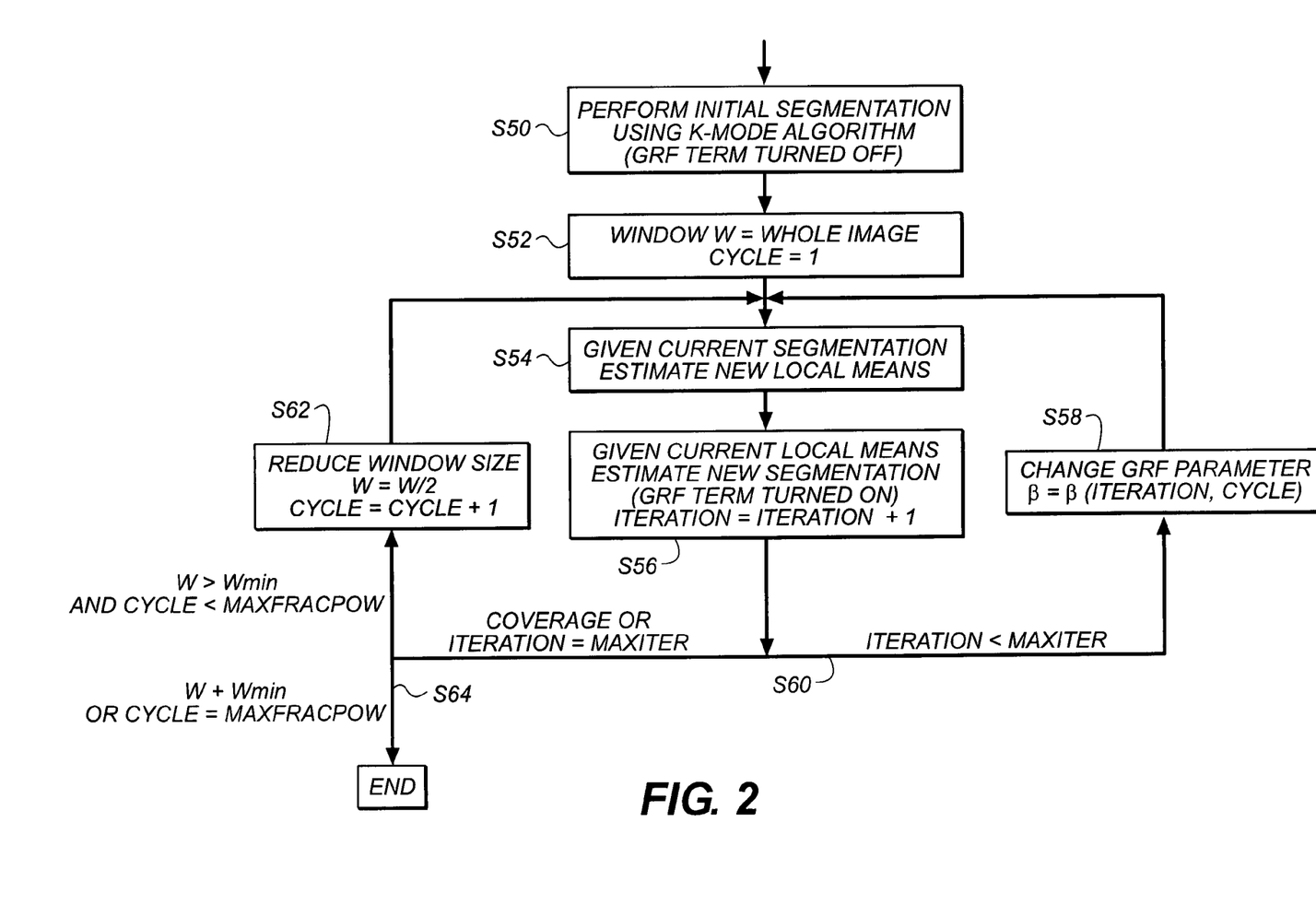
FIG. 2 is a block diagram illustrating steps of segmenting lesion regions from normal tissue regions.
Figure 3A:
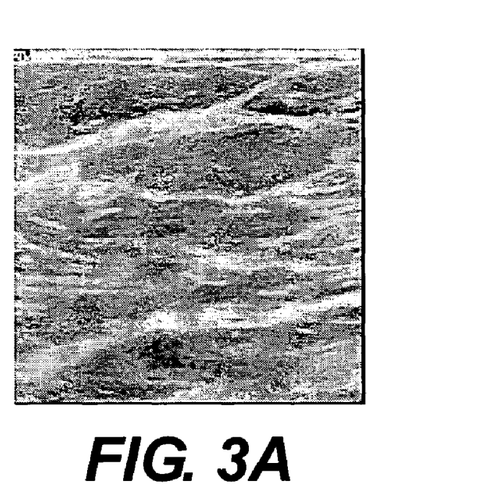
FIGS. 3A-3D are examples of ultrasound images comprising both lesion (benign and malignant) and normal tissue regions.
Figure 3B:
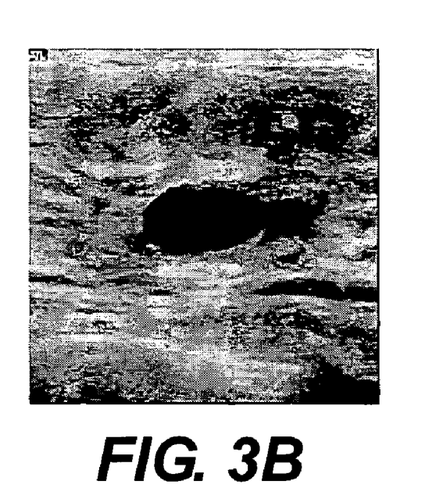
Figure 3C:
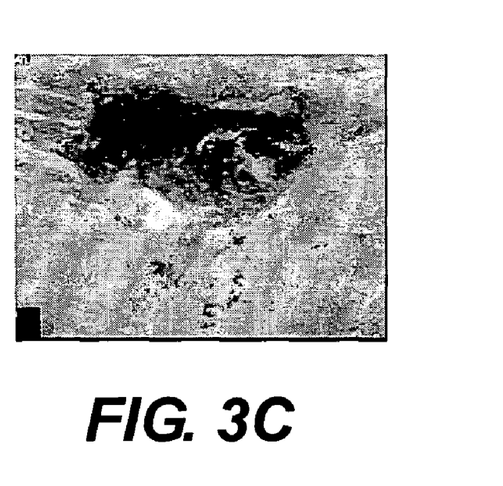
Figure 3D:
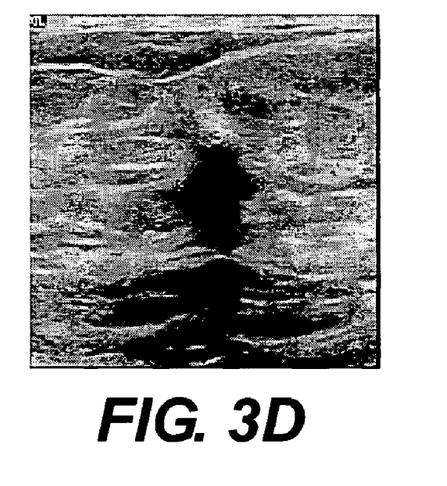
Figure 4A:
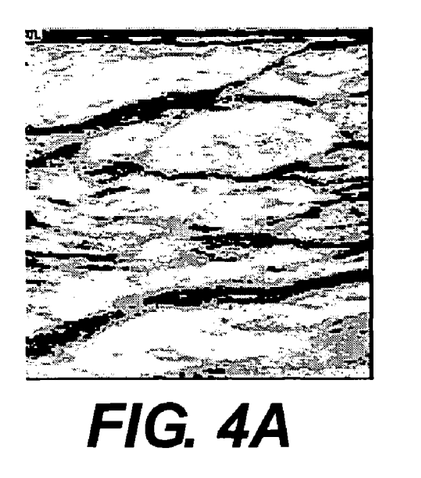
FIGS. 4A-4D correspond with FIGS. 3A-3D, and are examples of segmented lesion regions.
Figure 4B:
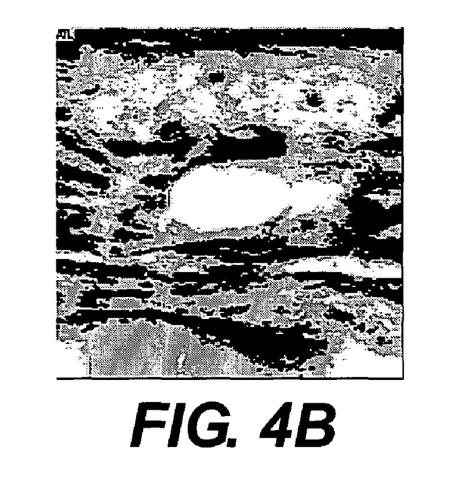
Figure 4C:
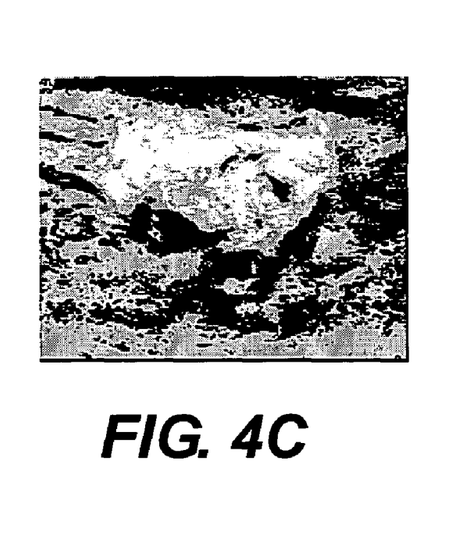
Figure 4D:
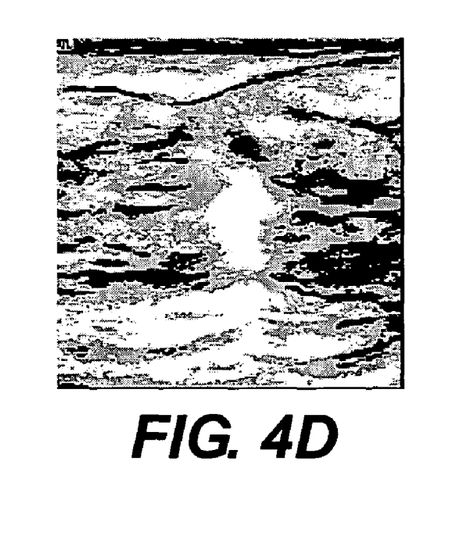

Referring now to FIG. 2, there is shown an block diagram of a suitable region segmentation method (step 20) according to a preferred embodiment of the present invention. The method is modified from the adaptive Bayesian color segmentation algorithm described in Luo et al., "Towards physics-based segmentation of photographic color images," Proceedings of the IEEE International Conference on Image Processing, 1997.

Region segmentation generates a tractable number of physically coherent regions, in terms of similar intensity patterns, of arbitrary shape.

Similar intensity patterns can refer to similar intensity values, or similar intensity textures, and/or a combination of both. The regions having similar intensity patterns fall into the same intensity class, but otherwise are spatially separated and have different shapes. Although this segmentation method is preferred, it will be appreciated that a person of ordinary skill in the art can use a different segmentation method to obtain regions of arbitrary shape without departing from the scope of the present invention. Segmentation of arbitrarily shaped regions facilitates accurate measurement of the size, location, shape, as well as internal characteristics of potential objects.

An initial segmentation of the image into regions is obtained S50. An intensity histogram of the image is computed and then partitioned into a plurality of clusters that correspond to distinctive, prominent intensities in the image. Each pixel of the image is classified to the closest cluster in the intensity space according to a preferred intensity distance metric with respect to the mean values of the intensity clusters (Luo et al., "Towards physics-based segmentation of photographic color images," Proceedings of the IEEE International Conference on Image Processing, 1997). This classification process results in an initial segmentation of the image.

A neighborhood window is placed at each pixel in order to determine what neighborhood pixels are used to compute the local intensity histogram for this pixel. The window size is initially set at the size of the entire image S52, so that the local intensity histogram is the same as the one for the entire image and does not need to be recomputed.

Next, an iterative procedure is performed between two alternating processes: re-computing S54 the local mean values of each intensity class based on the current segmentation, and re-classifying the pixels according to the updated local mean values of intensity classes S56.

This iterative procedure is performed until a convergence is reached S60. During this iterative procedure, the strength of the spatial constraints can be adjusted in a gradual manner S58 (for example, the value of $\beta$, which indicates the strength of the spatial constraints, is increased linearly with each iteration).

After a convergence is reached for a particular window size, the window used to estimate the local mean values for intensity classes is reduced by half in size S62.

The iterative procedure is repeated for the reduced window size to allow more accurate estimation of the local mean values for intensity classes. This mechanism introduces spatial adaptivity into the segmentation process.

Finally, segmentation of the image is obtained when the iterative procedure reaches convergence for the minimum window size S64.

In a preferred embodiment of the present invention, Applicants set/pre-defined the number of distinctive intensity classes to be 3, roughly corresponding to lesion, normal tissue, and unknown structure.

An advantage of the preferred segmentation method described in FIG. 2 is that small lesions are not lost because of its size, which is often a challenge for other non-preferred segmentation method, such as the well-known classic k-means algorithm. Without proper region segmentation, can be difficult to perform object recognition and proper assessment of such properties as size and shape.

The result of segmentation contains labels of regions, i.e., each pixel is represented by its label value. The image of labeled regions is referred to as a label image, or segmentation map.

As indicated above, it may be desirable to pre-process 15 the input image prior to region segmentation 20. More particularly, it may be desirable to enhance the contrast between lesion and normal tissues before segmentation 20 is applied.

In a preferred embodiment of the present invention, a gamma adjustment of 2.0 is used. Alternative contrast enhancement can be performed for the same purpose. Let I(x,y) denote an intensity value if a pixel coordinates (x,y), gamma adjusted value is given by the equation: I'(x,y)=I(x,y)^(1/gamma).

Following region segmentation 20, the segmented regions may be selected as candidate regions for lesions in step 30.

In general, lesions typically appear as relatively darker regions in an ultrasound image because they tend to form boundaries against the normal tissue and have higher water content. Therefore, darker regions are selected as lesion candidates in the present invention.

In a preferred embodiment of the present invention, regions with an average intensity lower than a pre-determined value, (for example, 20% of the possible maximum intensity) are selected as candidate regions.

Additional criteria can be used to further eliminate/reduce unlikely candidate regions. For example, it is assumed that an operator would usually place the lesion in the center of the view. In other words, a lesion, if present, would be completely contained in the image, therefore regions that touch image borders are unlikely to be the lesion and thus can be eliminated from further analysis.

Candidate selection facilitates the subsequent lesion classification by focusing on a small number of regions.

For each of the selected candidate regions, a set of features are extracted to characterize each region in step 40. The list of features can comprise one or more categories. In a particular application, three categories are employed: shape features, interior features, and boundary features. Other categories can be included, for example, shadow features. Other categories may be known to those skilled in the art.

In addition, raw measurements of features may be converted such that their values are normalized to be within [0, 1.0], by functions with appropriate nonlinearity characteristics. Normalization is well known for persons skilled in the art. Those who are skilled in the art can recognize alternative types of features, without departing from the scope and spirit of the present invention.

In general, lesions that have compact, elliptical shape and smooth contour tend to be benign.

The basic features are height, width, and perimeter, and size.

An aspect ratio of a region is the major axis/minor axis, or height over width, of the region. This feature detector is used to discount long narrow shapes from being considered a lesion. In addition, malignant lesions are harder to compress and may appear taller than wider along the direction of ultrasound scattering, i.e., the direction of the transducer. Benign lesions or non-lesions tend to appear as wider than taller. Such characteristics can be indicated by the aspect ratio as well.

The compactness is the square of the perimeter of the region divided by the area of region. A sigmoid belief function maps the circularity to a belief value.

The interior features include mean and standard deviation of the intensity values within the interior of a candidate region.

The boundary features include mean and standard deviation of the intensity gradient values along the boundary of a candidate region.

The shadow feature is used to measure the shadow cast by a candidate lesion region.

Once the particular features are computed for all the candidate regions, the features are used to classify whether a candidate region is a benign lesion, or a malignant lesion, or not a lesion at all, in step 50.

The third class of "not a lesion" is provided should the candidate selection step 30 occasionally include non-lesion regions to be selected because of an ambiguity. Examples of such cases, as classified by medical professionals, need to be collected as so-called training examples. The features and the associated classification labels of these training examples are the basis for deriving a classifier, which is then used to classify a novel candidate region not seen by the classifier. Those skilled in the art can choose from many existing classifiers, including a decision tree, a neural network, a Bayesian classifier, or the like. Duda, Hart, and Stork, "Pattern Classifier", describes examples of such classifiers. In a preferred embodiment of the present invention, a decision tree is used. If a confidence value is desired, alternative classifiers such as a neural network or a Bayesian classifier should be used.

Figure 5A:
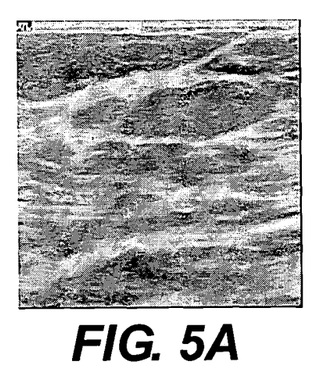
FIGS. 5A-5D correspond with FIGS. 3A-3D and FIGS. 4A-4D, and show examples of classified lesion regions.
Figure 5B:
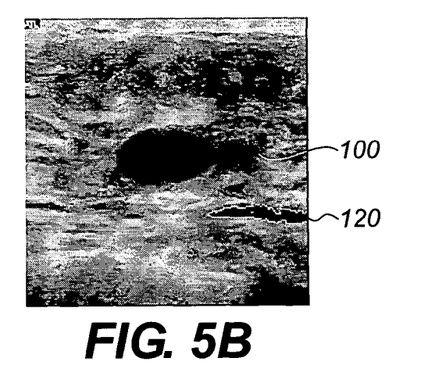
Figure 5C:
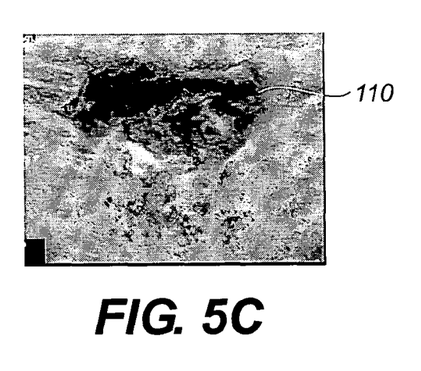
Figure 5D:
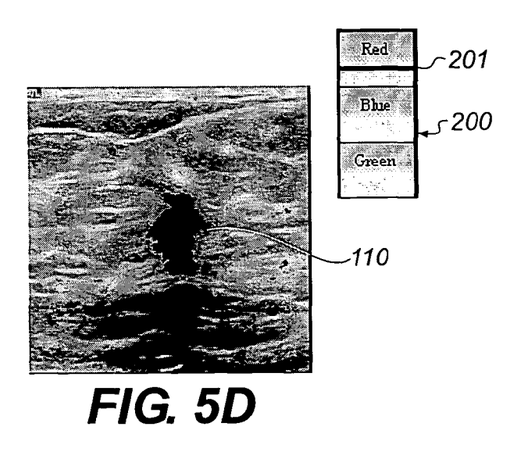

FIGS. 3A-3D shows four example ultrasound images of the breast. In FIGS. 4A-4D, corresponding to FIGS. 3A-3D, each image is segmented into three intensity classes, with the intensity class of the darkest regions indicated by the highest brightness in the segmented images. In general, lesion candidates are selected from these regions. In FIGS. 5A-5D, all the candidate regions are classified into benign (e.g., part 100), malignant (e.g., part 110), or not a lesion (e.g., part 120). More particularly, FIG. 5A shows no lesion, FIG. 5B shows a benign lesion, FIG. 5C shows a malignant lesion, and FIG. 5D shows a malignant lesion.

Alternatively, if a confidence value is desirable, a colored bar 200 (shown proximate FIGS. 5A-5D) can be displayed next to a region upon which the operator places the cursor, wherein the shades (color saturation) of the bar gives a visual presentation of the lesions classification and the associated confidence value. For example, a tick 201 (or other symbol) could point to the range of deep red of the color bar when the lesion is classified as malignant with a high confidence value, or the range of light blue of the color bar when lesion is classified as benign but with a low confidence value, or the like.

Figure 6A:
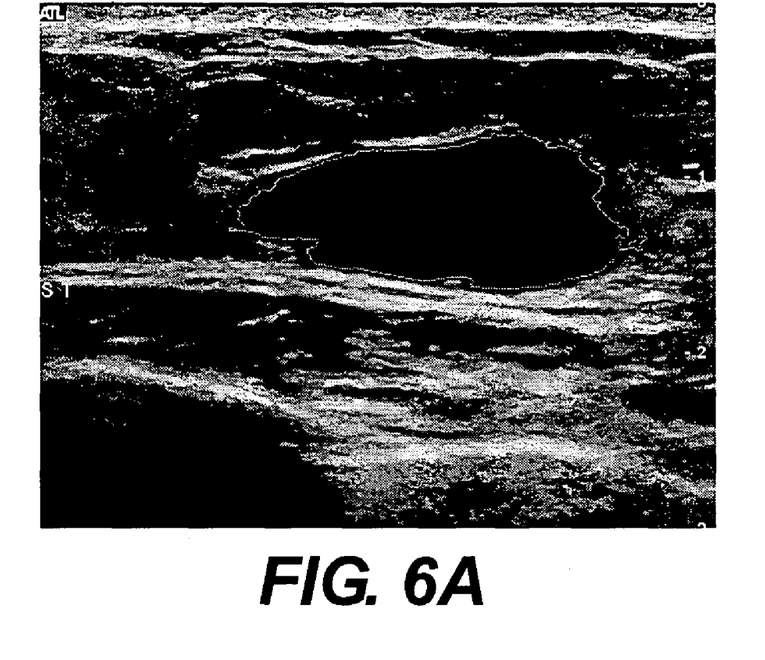
FIGS. 6A and 6B shows additional examples of classified lesion regions.
Figure 6B:
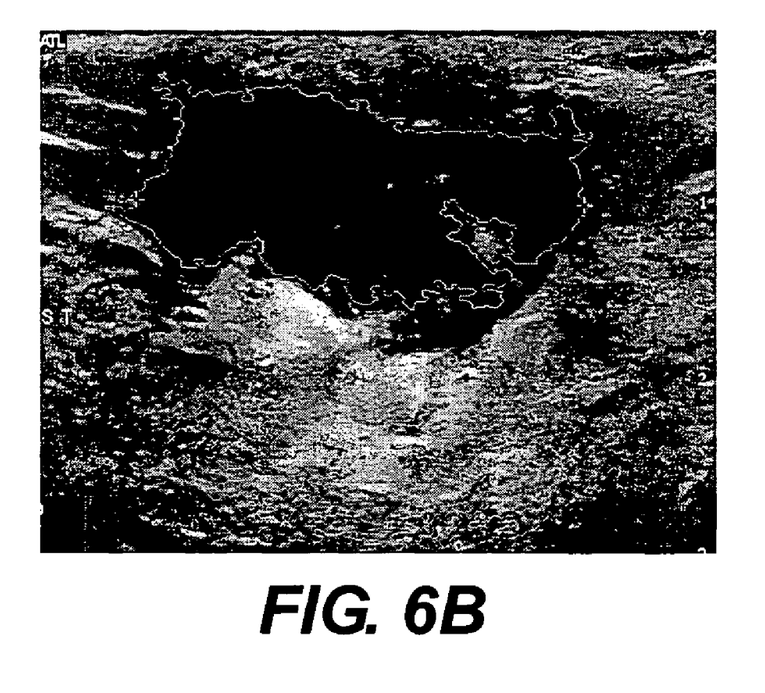

FIGS. 6A and 6B provide additional examples, showing a cursor operable by an operator and wherein a candidate region is outlined.

Although the present invention is described in a preferred embodiment that is related to lesions in the breast, it will be understood that variations and modifications can be effected within the spirit and scope of the invention for lesions in other tissues, such as the liver.

The present invention may be practiced online, real-time, or offline. In the real-time situation, it could provide the operator with instant warning or feedback. In the offline situation, it could analyze a database of pre-recorded images.

In addition, it may be desirable to display the ultrasound image and an outline of the segmented lesion region following automatic segmentation, and accept adjustment of the region outline by an operator using a graphical user interface.

The present invention may be implemented for example in a computer program product. A computer program product may include one or more storage media, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The system of the invention includes a programmable computer having a microprocessor, computer memory, and a computer program stored in said computer memory for performing the steps of the method. The computer has a memory interface operatively connected to the microprocessor. This can be a port, such as a USB port, over a drive that accepts removable memory, or some other device that allows access to camera memory. The system includes a digital camera that has memory that is compatible with the memory interface. A photographic film camera and scanner can be used in place of the digital camera, if desired. A graphical user interface (GUI)

and user input unit, such as a mouse and keyboard can be provided as part of the computer.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for detecting a lesion in an input digital ultrasound image of anatomical tissue, the method being carried out by a digital computer including a computer readable storage medium storing a computer program of the method, the method comprising steps of:
    accessing the input digital ultrasound image of anatomical tissue;
    segmenting spatially contiguous pixels in the input digital ultrasound image into a plurality of regions in accordance with substantially similar intensity patterns, the segmenting step including substeps of:
        segmenting the input digital ultrasound image into regions by computing an intensity histogram,
        partitioning the histogram into a plurality of clusters that correspond to distinctive prominent intensities in the input digital ultrasound image,
        classifying each pixel of the input digital ultrasound image to the closest cluster as a function of the mean values of the intensity clusters;
        placing a neighborhood window at each pixel in order to determine what neighborhood pixels are used to compute a local intensity histogram for the pixel, wherein an initial neighborhood window size is set at the size of the entire input digital ultrasound image,
        recomputing local mean values of each intensity class based on the current segmentation,
        reclassifying the pixels according to the recomputed local mean values of intensity classes,
        repeating the recomputing and reclassifying substeps until a convergence is reached, and
        repeating the placing, recomputing, reclassifying and repeating substeps for one or more reduced neighborhood window sizes, until segmentation of the input digital ultrasound image is obtained when a minimum window size is processed;
    selecting, from the plurality of regions, one or more candidate lesion regions having an intensity value lower than a pre-determined intensity value; and
    classifying the one or more candidate lesion regions into at least one of the following classes: benign, malignant, or unknown.

2. The method of claim 1, wherein the step of classifying the one or more candidate lesion regions includes the steps of:
    classifying the one or more candidate lesion regions into the benign or malignant class in accordance with at least one of the following features: a shape feature, an interior feature, or a boundary feature.

3. The method of claim 1, further comprising the step of providing a confidence value for the lesion classification.

4. The method of claim 1, further comprising the step of, prior to the step of segmenting, pre-processing the input digital ultrasound image.

5. The method of claim 4, wherein the input digital ultrasound image comprises a lesion, and the input digital ultrasound image is pre-processed to enhance the contrast between the lesion and the normal anatomical tissue.

6. The method of claim 1, wherein the selected candidate lesion regions have an average intensity value lower than a pre-determined intensity value.

7. A method of determining a candidate lesion region within an input digital ultrasound image of anatomical tissue the method being carried out by a digital computer including a computer readable storage medium storing a computer program of the method, the method comprising steps of:
    accessing the input digital ultrasound image of anatomical tissue;
    segmenting spatially contiguous pixels in the input digital ultrasound image into a plurality of regions in accordance with substantially similar intensity values and spatial smoothness constraints, the segmenting step including substeps of:
        segmenting the input digital ultrasound image into regions by computing an intensity histogram,
        partitioning the histogram into a plurality of clusters that correspond to distinctive prominent intensities in the input digital ultrasound image,
        classifying each pixel of the input digital ultrasound image to the closest cluster as a function of the mean values of the intensity clusters;
        placing a neighborhood window at each pixel in order to determine what neighborhood pixels are used to compute a local intensity histogram for the pixel, wherein an initial neighborhood window size is set at the size of the entire input digital ultrasound image,
        recomputing local mean values of each intensity class based on the current segmentation,
        reclassifying the pixels according to the recomputed local mean values of intensity classes,
        repeating the recomputing and reclassifying substeps until a convergence is reached, and
        repeating the placing, recomputing, reclassifying and repeating substeps for one or more reduced neighborhood window sizes, until segmentation of the input digital ultrasound image is obtained when a minimum neighborhood window size is processed; and
    selecting, from the plurality of regions, one or more candidate lesion regions having an intensity value lower than a pre-determined intensity value.

8. The method of claim 7, further comprising the step of, prior to segmenting, pre-processing the input digital ultrasound image such that a contrast between a lesion and normal anatomical tissue would be enhanced.

9. The method of claim 8, where in the step of pre-processing comprises a gamma adjustment.

10. The method of claim 7, further comprising the step of classifying the one or more candidate lesion region into at least one of the following classes: benign, malignant, or unknown.

11. The method of claim 10, wherein the step of classifying the one or more candidate lesion regions includes the steps of:
    classifying the one or more candidate lesion region into the benign or malignant class in accordance with at least one of the following features: a shape feature, an interior feature, or a boundary feature.

12. The method of claim 10, wherein the step of classifying further comprises steps of:
    extracting an outline of the selected candidate lesion region;
    determining at least one feature from the group: a shape feature, an interior feature, or a boundary feature; and
    classifying the selected candidate lesion region as either benign, malignant, or unknown or malignant in response to the computed at least one feature.

13. The method of claim 12, wherein at least two features are determined for the selected candidate lesion region.

14. The method of claim 12, wherein the shape feature is an aspect ratio of the selected candidate lesion region.

15. The method of claim 7, further comprising the step of: displaying the input digital ultrasound image on a display with an outline of the selected candidate lesion region.

16. A system for detecting a lesion in an input digital ultrasound image of anatomical tissue, the system including a digital computer comprising:
  a computer readable storage medium having stored therein medical image data and digital data processor programs; and
  a digital data processor coupled to the storage medium, whereby the processor is configured to:
  access the input digital ultrasound image of anatomical tissue;
  segment spatially contiguous pixels in the input digital ultrasound image into a plurality of regions in accordance with substantially similar intensity patterns; by
    segmenting the input digital ultrasound image into regions by computing an intensity histogram,
    partitioning the histogram into a plurality of clusters that correspond to distinctive prominent intensities in the input digital ultrasound image,
    classifying each pixel of the digital image to the closest cluster as a function of the mean values of the intensity clusters,
    placing a neighborhood window at each pixel in order to determine what neighborhood pixels are used to compute a local intensity histogram for the pixel, wherein an initial neighborhood window size is set at the size of the entire input digital ultrasound image,
    recomputing local mean values of each intensity class based on the current segmentation,
    reclassifying the pixels according to the recomputed local mean values of intensity classes,
    repeating the recomputing and reclassifying substeps until a convergence is reached, and
    repeating the placing, recomputing, reclassifying and repeating for one or more reduced neighborhood window sizes, until segmentation of the input digital ultrasound image is obtained when a minimum neighborhood window size is processed;
  select from the plurality of regions, one or more candidate lesion regions having an intensity value lower than a pre-determined intensity value; and
  classify the one or more candidate lesion regions into at least one of the following classes: benign, malignant, or unknown.

17. A method for detecting a lesion in an input digital ultrasound image of anatomical tissue, the method being carried out by a digital computer including a computer readable storage medium storing a computer program of the method, the method comprising steps of:
  accessing the input digital ultrasound image of anatomical tissue;
  segmenting spatially contiguous pixels in the input digital ultrasound image into a plurality of regions in accordance with substantially similar intensity patterns, the segmenting step including substeps of:
    segmenting the input digital ultrasound image into regions by computing an intensity histogram,
    partitioning the histogram into a plurality of clusters that correspond to distinctive prominent intensities in the input digital ultrasound image,
    classifying each pixel of the input digital ultrasound image to the closest cluster as a function of the mean values of the intensity clusters;
    placing a neighborhood window at each pixel in order to determine what neighborhood pixels are used to compute a local intensity histogram for the pixel, wherein an initial window size is set at the size of the entire input digital ultrasound image,
    recomputing local mean values of each intensity class based on the current segmentation,
    reclassifying the pixels according to the recomputed local mean values of intensity classes,
    repeating the recomputing and reclassifying substeps until a convergence is reached, and
    repeating the placing, recomputing, reclassifying and repeating substeps for one or more reduced neighborhood window sizes, until segmentation of the input digital ultrasound image is obtained when a minimum neighborhood window size is processed;
  selecting, from the plurality of regions, one or more candidate lesion regions having an intensity value lower than a pre-determined intensity value;
  eliminating from the selected candidate lesion regions any regions that touch image borders; and
  classifying the one or more selected candidate lesion regions into at least one of the following classes: benign, malignant, or unknown.

18. A method of determining a candidate lesion region within an input digital ultrasound image, the method being carried out by a digital computer including a computer readable storage medium storing a computer program of the method, the method comprising steps of:
  accessing the input digital ultrasound image of anatomical tissue;
  segmenting spatially contiguous pixels in the input digital ultrasound image into a plurality of regions in accordance with substantially similar intensity values and spatial smoothness constraints, the segmenting step including substeps of:
    segmenting the input digital ultrasound image into regions by computing an intensity histogram,
    partitioning the histogram into a plurality of clusters that correspond to distinctive prominent intensities in the input digital ultrasound image,
    classifying each pixel of the input digital ultrasound image to the closest cluster as a function of the mean values of the intensity clusters;
    placing a neighborhood window at each pixel in order to determine what neighborhood pixels are used to compute a local intensity histogram for the pixel, wherein an initial neighborhood window size is set at the size of the entire input digital ultrasound image,
    recomputing local mean values of each intensity class based on the current segmentation,
    reclassifying the pixels according to the recomputed local mean values of intensity classes,
    repeating the recomputing and reclassifying substeps until a convergence is reached, and
    repeating the placing, recomputing, reclassifying and repeating substeps for one or more reduced neighborhood window sizes, until segmentation of the input digital ultrasound image is obtained when the minimum window size is processed;
  selecting, from the plurality of regions, one or more candidate lesion regions having an intensity value lower than a pre-determined intensity value; and
  eliminating from the selected candidate lesion regions any regions that touch image borders.

* * * * *